(12) United States Patent
Simmons et al.

(10) Patent No.: US 7,695,444 B1
(45) Date of Patent: Apr. 13, 2010

(54) FLEXIBLE PROTECTIVE COVER FOR PREVENTING FLUID FROM ENTERING AN OPEN EPIDERMAL SITE

(76) Inventors: Kathy A. Simmons, 25323 Intrepid La., Galveston, TX (US) 77554; Mary E. Simmons, 25323 Intrepid La., Galveston, TX (US) 77554

( * ) Notice: Subject to any disclaimer, the term of this patent is extended or adjusted under 35 U.S.C. 154(b) by 39 days.

(21) Appl. No.: 11/857,004

(22) Filed: Sep. 18, 2007

(51) Int. Cl.
*A61F 13/00* (2006.01)
*A61F 5/00* (2006.01)
*A61F 5/44* (2006.01)

(52) U.S. Cl. .............................. 602/79; 602/41; 602/42; 602/43; 602/44; 602/78; 602/3; 128/888; 128/889; 128/849; 128/850; 128/851; 128/852; 128/853; 128/893; 128/894; 128/96.1; 128/99.1; 128/100.1; 128/105.1; 604/304; 604/305; 604/306; 604/307; 604/308; 604/309; 604/310; 604/311; 604/312; 604/313; 604/338; 604/353; 604/355; 604/164.08; 604/192; 604/263; 604/327; 604/332; 604/337; 206/438; 206/440; D24/190; D24/189; 24/572.1; 2/908

(58) Field of Classification Search ............. 602/41–44, 602/79, 78, 3; 604/46, 192, 289, 304–316, 604/164.08, 263, 327, 332, 337–338, 353, 604/355, 303, 179–180, 174; 128/888–889, 128/849–853, 893–894, 96.1, 99.1, 100.1, 128/105.1; 206/438, 440; 2/908; D24/190, D24/189; 24/572.1
See application file for complete search history.

(56) References Cited

U.S. PATENT DOCUMENTS

| | | | | |
|---|---|---|---|---|
| 2,367,690 A | * | 1/1945 | Purdy | 128/888 |
| 3,234,941 A | * | 2/1966 | Tucker | 128/888 |
| 3,520,306 A | * | 7/1970 | Gardner et al. | 606/215 |
| 5,817,038 A | * | 10/1998 | Orange et al. | 602/3 |
| 6,987,209 B2 | * | 1/2006 | Augustine et al. | 602/42 |
| 2001/0029956 A1 | * | 10/2001 | Argenta et al. | 128/897 |
| 2003/0120194 A1 | * | 6/2003 | Stapf | 602/48 |
| 2003/0139696 A1 | * | 7/2003 | Boukanov et al. | 602/41 |
| 2007/0191754 A1 | * | 8/2007 | Aali | 602/58 |

FOREIGN PATENT DOCUMENTS

JP 2000116691 A * 4/2000

OTHER PUBLICATIONS

English Translation of JP 2000116691 A.*

* cited by examiner

*Primary Examiner*—Patricia M Bianco
*Assistant Examiner*—Tarla R Patel
(74) *Attorney, Agent, or Firm*—Buskop Law Group, P.C.; Wendy Buskop

(57) ABSTRACT

A flexible protective cover for preventing fluid from entering an open epidermal site on a user, comprising: a central portion having at least one rib, an edge connected to the central portion at an angle, a lip disposed around the edge, a sealing member disposed over the lip for providing a sealing engagement between the lip and the open epidermal site, and at least one adjustable strap removably connected to the central portion. Also disclosed is a flexible protective cover having a central portion, an edge connected to the central portion at an angle, an inflatable sealing member integral with the edge for providing the sealing engagement, and at least one adjustable strap removably connected to the central portion.

25 Claims, 6 Drawing Sheets

FLEXIBLE PROTECTIVE COVER FOR PREVENTING FLUID FROM ENTERING AN OPEN EPIDERMAL SITE

FIELD

The present embodiments relate to a flexible protective cover for preventing fluid from entering an open epidermal site

BACKGROUND

A need exists for a protective cover for an open epidermal site that can form a water-tight seal to effectively prevent fluid from entering the open epidermal site.

A further need exists for a protective cover that is flexible and able to form a seal on various parts of a human or animal body.

A need also exists for a protective cover having sufficient strength or reinforcement means for maintaining a seal and preventing contact with an open epidermal site when touched or impacted by light or moderate pressure.

A need exists for a protective cover having adjustable means for securing to various parts of a human or animal body and for securing to various types and sizes of humans and animals.

The present embodiments meet these needs.

BRIEF DESCRIPTION OF THE DRAWINGS

The detailed description will be better understood in conjunction with the accompanying drawings as follows.

Figure 1:
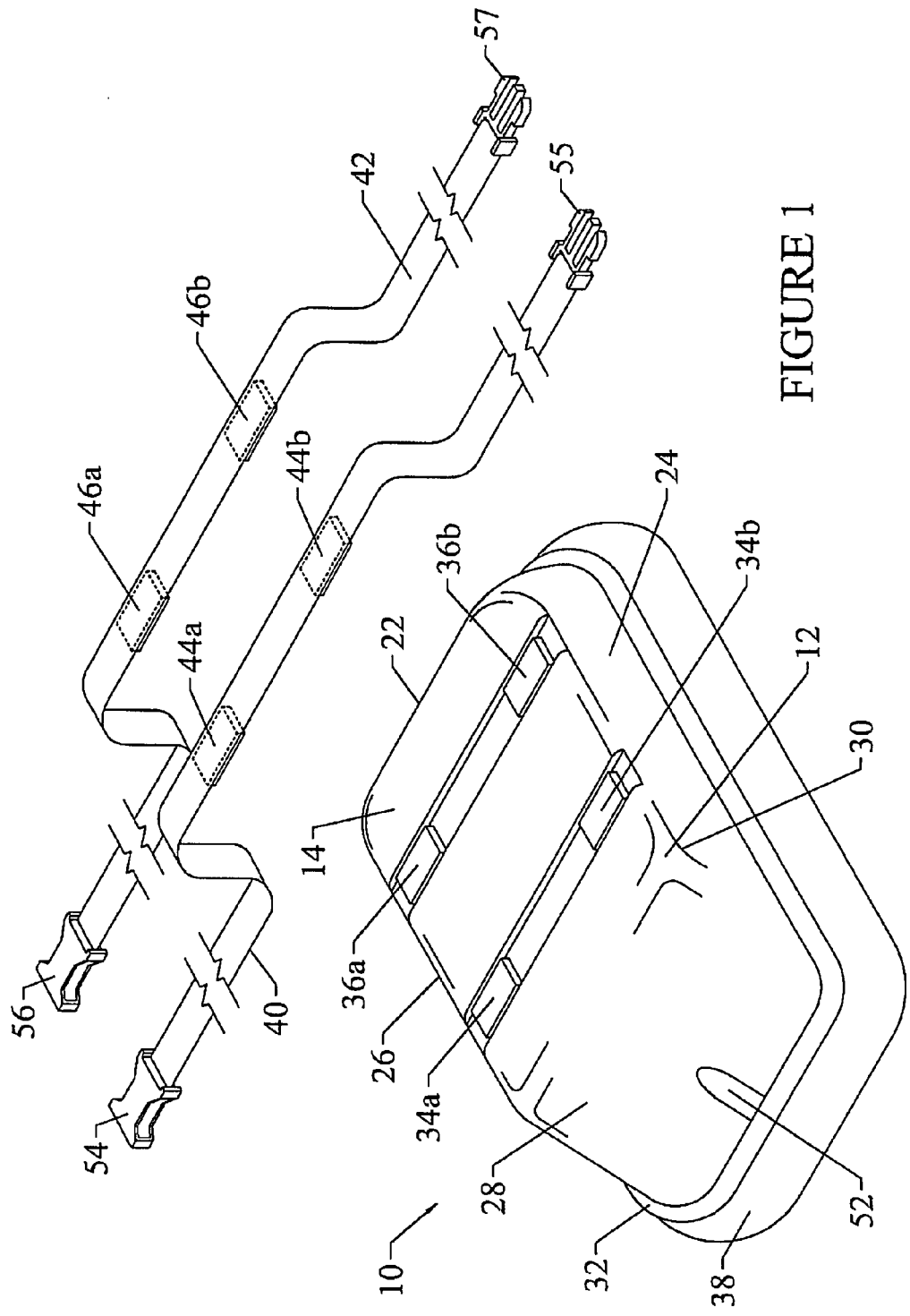
FIG. 1 depicts a perspective view of the outside surface of an embodiment of the present flexible protective cover.

The present embodiments are detailed below with reference to the listed figures.

DETAILED DESCRIPTION OF THE EMBODIMENTS

Before explaining the present apparatus in detail, it is to be understood that the apparatus is not limited to the particular embodiments and that it can be practiced or carried out in various ways.

The present embodiments relate to a flexible protective cover for preventing fluid from entering an open epidermal site on a user.

The present flexible protective cover advantageously provides the dual benefits of both physically protecting an open epidermal site from contact and forming a water-tight seal for preventing fluid from entering the open epidermal site.

The protection of an open epidermal site, such as a surgical site, a catheter entry or exit site, or the site of an intravenous line, is accomplished by physically covering the open epidermal site while maintaining a space between the flexible protective cover and the open epidermal site, thereby preventing pain, irritation, injury, and infection that can be caused through accidental contact. The flexible protective cover can be made from a sturdy material and can have reinforcement means, such as interior ribs and spacers, to prevent the flexible protective cover from deforming under light or moderate pressure caused by contact.

The prevention of fluid entry into an open epidermal site is accomplished using a sealing member that provides a sealing engagement between the flexible protective cover and the open epidermal site. The sealing engagement allows a human or animal with a wound or similar open epidermal site to bathe, shower, or possibly swim normally, and to withstand exposure to rain and other precipitation without allowing the entry of fluid into the open epidermal site. The prevention of fluid from entering an open epidermal site can prevent pain, irritation, injury, and infection, and can prevent a wound dressing, such as Tegaderm™, from becoming wet, necessitating frequent dressing changes. Further, the ability to bathe and shower normally allows an individual to maintain proper hygiene and morale, to avoid further illnesses or infections caused by improper hygiene, or possible contamination of sterile environments, such as hospitals, caused by improper hygiene.

The present flexible protective cover is advantageously made from a flexible material, such as a silicone-based material. The flexibility of the present flexible protective cover allows open epidermal sites on any part of a human or animal body to be effectively covered and sealed to prevent fluid entry. Further, the flexible material can be a non-irritating, non-toxic, hypoallergenic, recyclable material, thereby allowing any individual, including individuals with allergies or sensitivities to certain materials, to wear the present flexible protective cover without experiencing irritation or allergic reaction.

The present flexible protective cover can further advantageously include adjustable securing means, such as straps with fasteners, allowing the flexible protective cover to be worn by humans or animals of any size or to be secured to body parts of any size.

The present flexible protective cover can additionally have any shape, including shapes suitable for promoting entertainment, comfort, education, or proper hygienic behaviors among children, such as shapes of cartoon characters. The shape of the present flexible cover can also be functional, to allow protection of uniquely shaped open epidermal sites, or open epidermal sites on locations of the body that are otherwise difficult to protect.

Further, the present flexible cover can include engagement means, such as a slit within an interior spacer and one or more openings within an edge, for engaging and securing a tube, intravenous line, catheter, or other medical tubing while covering the open epidermal site. This securing can prevent irritation and injury caused by motion of the medical equipment, and can also prevent damage or malfunction of the medical equipment, such as kinks or leaks in a line or tube, caused by movement or contact with medical equipment.

The flexible protective cover includes a one-piece flexible cover body for covering an open epidermal site, which can include a dressing, a catheter, an intravenous medical line, a surgical incision site, an intravenous line point of entry, a peripheral intravenous line point of entry, a port for central venous access, a central venous line point of entry, a catheter line point of entry, a boil, a blister, a wound, one or more sutures, or combinations thereof. The open epidermal site can be disposed on any creature, including a human, a horse, a cow, or a similar domestic animal.

The one-piece flexible cover body can have any shape or dimensions, such as a rectangular body ranging from about two inches to about twelve inches in length, about one inch to about eight inches in width, and about one half inch to about six inches in height. For example, the one-piece flexible cover body could have a length of twelve inches and a width of two inches to cover a long surgical incision in the abdomen, or a length of twelve inches and a width of eight inches to cover a twelve inch by eight inch wound dressing. The height of the one-piece flexible cover body can vary to accommodate pieces of medical equipment, such as catheters, or thick dressings, such as bandages having a thickness of four inches or more.

It is also contemplated that the one-piece flexible cover body can be round, such as circle having a diameter ranging from about two inches to about twelve inches or an elliptical shape having a length of about two inches and a width of about 1.5 inches for covering an eye after surgery. Round-shaped one-piece flexible cover bodies can also include oblong shapes, oval shapes, elliptical shapes, or other rounded shapes, such as polygons with rounded corners.

In an embodiment, the one-piece flexible cover body can have a cartoon shape, such as "Spongebob Squarepants"™ for providing enjoyment and comfort to child-aged users. "Cartoon-shaped" one-piece flexible cover bodies can include the shape of any article, including plants, animals, sport symbols, logos, equipment, cartoon characters, famous persons, polygons, other similar shapes, parts thereof, and combinations thereof.

The one-piece cover body can also have an irregular shape to facilitate covering an irregularly shaped open epidermal site, or an open epidermal site on a location on a body that is difficult to protect.

The one-piece flexible cover body can be made from a non-irritating, non-toxic, hypoallergenic, recyclable, silicone based material, such as innocuity silica gel. Use of innocuity polyvinylchloride is also contemplated. The material is contemplated to be latex-free to promote hypoallergenic qualities. It is contemplated that the material of the one-piece flexible cover body can have a rigidity of 90 degrees. The material can be white, or the material can be provided with one or more colors. It is also contemplated that the one-piece flexible cover body can be decorated, such as by applying one or more adhesive decorations, paints, molds adhered to the outside surface, or similar materials.

In an embodiment, the one-piece flexible cover body can include an edge made from a bendable, shapeable material, such as a 24" Flexible Curve made by the C-Thru® Ruler Company of Bloomfield, Conn., to allow the flexible protective cover to be provided with any shape, as needed, to cover an open epidermal site having an irregular shape, or an open epidermal site on a location on a body that is difficult to protect. The shapeable material is contemplated to be non-brittle, generally stiff, and provide horizontal shaping, as opposed to vertical shaping. It is preferred that the shape of the material is bidirectional on a X-axis, without being deformable along a Y-axis. The shapeable material can have a thickness ranging from about 0.25 inches to about 1 inch. In an embodiment, the shapeable material can have a core that is encapsulated with a softer thermoplastic or a blend of thermoplastic with elastomer.

In yet another embodiment, the core of the shapeable material could be encapsulated with a sealing material, enabling the shapeable bendable material to provide the dual functionality of forming a shape for the flexible protective cover and forming the fluid-tight seal without the need for a separate edge and sealing member. Use of this shapeable sealing material can also advantageously eliminate the need for adhesives, which can cause allergic reactions in certain users.

The one-piece flexible cover body includes a central portion having an outside surface and an inside surface. The central portion can have a thickness ranging from about 0.125 inches to about 0.5 inches, as needed to provide strength and stability to protect an open epidermal site from contact. In an embodiment, the central portion can made from a very thin material, such as a flexible plastic, rubber, or silicone barrier.

One or more ribs can extend along the inside surface of the central portion for preventing deformation of the central portion, such as deformation caused by accidental contact or impact. Any number of ribs can be used to reinforce the central portion, such as two parallel ribs integrally molded to the inside surface of the central portion that have a length equal to a dimension of the central portion, a width ranging from about 0.5 inches to about 2 inches, and a thickness ranging from about 0.125 inches to about 0.5 inches. In a contemplated embodiment, from one to six ribs can be integrally molded to the inside surface of the central portion. It is also contemplated that the ribs can be made from a different material than the central portion, such as a stiff plastic, to provide added strength and resistance to deformation.

In an embodiment, the central portion can also include one or more spacers integral with the inside surface of the central portion and horizontal to one or more of the ribs, which can provide additional reinforcement for preventing deformation of the central portion. It is contemplated that a spacer can have a depth slightly larger than that of the ribs, and any width, such as about 0.125 inches. It is contemplated that up to four spacers can be integral with the inside surface, depending on the size of the one-piece flexible cover body. Each spacer can also include a slit for securely engaging tubing or other medical equipment connected to the open epidermal site. The slit can have a width ranging from about 0.125 inches to about 1 inch. It is contemplated that the width or diameter of the slit can be slightly smaller than the diameter of the tubing to ensure a secure, fluid-tight fit.

The one-piece flexible cover body can additionally include an edge secured at an angle to the central portion. In an embodiment, the one-piece flexible cover body can have multiple edges, each secured to the central portion at a different angle.

A rectangular embodiment can have a top edge, a first side edge, and a second side edge, each secured substantially perpendicular to the central portion, and an angular edge secured to the central portion at an angle, which can range from ten degrees to ninety degrees. Each edge can have a thickness ranging from about 0.125 inches to about 0.5 inches, or thicker if additional thickness is needed to provide strength and stability to the one-piece flexible cover body. It is contemplated that each edge can have a depth ranging from about 0.5 inches to about 4 inches, as needed to accommodate thick dressings or bandages. In an embodiment, one or more edges can include an opening, such as a slit, a cut, a hole, or a similar aperture having a diameter ranging from about 0.125 inches to about 1 inch, for securely engaging, in a force fit, tubing or other medical equipment connected to the open epidermal site. It is contemplated that the diameter of the opening can be slightly smaller than the diameter of the tubing to ensure a secure, fluid-tight fit.

A round one-piece flexible cover body can have a single edge encircling the central portion and connected substantially perpendicular to the central portion. Portions of the edge can be connected to the central portion at an angle.

One-piece flexible cover bodies having other shapes, such as cartoon shapes, can have similar edge configurations, encircling the perimeter of the central portion and connected substantially perpendicular to the central portion, or at an angle to the central portion. The edges can include one or more openings, as described previously, for securely engaging tubing or other medical equipment.

In an embodiment, the one or more openings can be defined by a groove, an outline, or a perforated section of the edge that can be selectively cut to create the opening.

A lip can be disposed around each of the edges. The lip can have a width slightly wider than that of the edges. The lip includes a sealing member for providing a sealing engagement between the lip and the open epidermal site. The sealing engagement is contemplated to be water-tight, able to prevent fluid from entering the open epidermal site.

In an embodiment, the sealing member can include a deformation resistant tubing, that can reassume its shape after light compression. The deformation resistant tubing can be made from flexible, compressible plastic or silicone, or other non-latex materials, having an inner diameter of up to three inches.

It is further contemplated that the sealing member can include inflatable tubing, such as a pre-inflated Cuff™ made by Laerdal or a Pocket Mask Seal made by Ambu™, having one or more valves used to inflate the tubing after compression. The inflation of the tubing can seal gaps between the central portion and the open epidermal site. In an embodiment, the one or more valves can be removable valves that are removed after inflation. It is also contemplated that a pre-inflated inflatable sealing member can be used.

One or more adjustable straps can be secured to the outside surface of the one-piece flexible cover body and used for securing the present flexible protective cover over an open epidermal site. The adjustable straps can have any length, such as about two inches to about six inches for securing around the wrist of a child, or ten feet or more to secure around the midsection of a horse. The adjustable straps can have any width, ranging from about 0.5 inches to about 4 inches or more.

The adjustable straps can be made from webbed materials, textiles, hypoallergenic materials, elastic materials, such as Stretchrite Polyester Non-Roll WaistBand Elastic made by Dyno Merchandise of Pompano Beach, Fla., or combinations thereof. In an embodiment, the adjustable straps can include buckles, slidable fasteners, or other similar fastening or tightening means for enabling the adjustable straps to be cinched to a user. It is contemplated that the buckles can include plastic or metal buckles having snapping or locking means with a quick release, pegs and holes, and other types of buckles or tightening means.

In an embodiment, one or more fasteners can be removably adhered to the outside of the central portion. The fasteners and means for engaging the fasteners can include loops and hooks of a hook and loop fastening material, such as Velcro™. Use of other similar fastening means, such as reusable adhesive, snaps, or loops of plastic or another material molded to the central portion, can also contemplated.

In an embodiment, at least two adjustable straps can engage a first fastening strap and a second fastening strap, which provide pressure to the outside surface of the cover body to create a fluid-tight seal. The first and second fastening straps can engage fasteners disposed on the outside surface of the cover body while the adjustable straps secure the cover body to the user.

In an alternative embodiment, the present flexible cover can include a one-piece flexible cover body having any shape and corresponding edges, as described previously. However, in lieu of a lip encircling the edges, this embodiment can include an inflatable sealing member integral with each of the edges providing a sealing engagement between the central portion and the open epidermal site.

It is contemplated that this embodiment can include one or more fasteners integral with the outside of the central portion, such as loops of plastic molded to the central portion, for engaging at least one adjustable straps to secure the one-piece flexible protective cover over the open epidermal site.

Referring now to FIG. 1, a perspective view of an outside surface (14) of an embodiment of the present flexible protective cover is shown.

FIG. 1 depicts a one-piece flexible cover body (10) with a central portion (12) having outside surface (14). Central portion (12) is connected substantially perpendicular to a top edge (22), a first side edge (24), and a second side edge (26). Central portion (12) is connected at an angle (30) to an angular edge (28). Angle (30) can be any angle, including angles ranging from ten degrees to ninety degrees. Thus, in an embodiment, angular edge (28) can also be connected substantially perpendicular to central portion (12).

A lip (32) is disposed around top edge (22), first side edge (24), second side edge (26), and angular edge (28), for engaging a sealing member (38). While FIG. 1 depicts sealing member (38) as deformation resistant tubing, other sealing members such as plastic-coated metal, inflatable tubing, and similar plastic, rubber, polymer, or other materials able to form a fluid-tight seal on a user are also contemplated.

Angular edge (28) is depicted having an opening (52) for securely engaging tubing or similar medical equipment connected to an open epidermal site beneath one-piece flexible cover body (10).

Outside surface (14) is depicted having a first anchored portion (34a) and a second anchored portion (34b) of a first fastener, and a first anchored portion (36a) and a second anchored portion (36b) of a second fastener. While FIG. 1 depicts a first and second fastener each having two anchored portions, any number of fasteners having any number of anchored portions can be used. Use of other fastening means lacking anchored portions is also contemplated. In an embodiment, use of fasteners can be omitted.

A first adjustable strap (40) and a second adjustable strap (42) are shown disengaged from one-piece flexible cover body (10). First adjustable strap (40) has a first means (44a) for engaging first anchored portion (34a) of the first fastener. First adjustable strap (40) also has a second means (44b) for engaging second anchored portion (34b) of the first fastener. Second adjustable strap (42) has a first means (46a) for engaging first anchored portion (36a) of the second fastener. Second adjustable strap (42) also has a second means (46b) for engaging second anchored portion (36b) of the second fastener.

While first adjustable strap (40) and second adjustable strap (42) are depicted each having two means for engaging two anchored portions of two fasteners, any number of fasteners or other removable fastening means can be used. It is also contemplated that first adjustable strap (40) and second adjustable strap (42) can be tightened over one-piece flexible cover body (10) without the use of fasteners.

First adjustable strap (40) has a first buckle (54) and a means for engaging first buckle (55), which can include any type of locking means with a quick release mechanism, pegs and holes, or other similar engagement means. Second adjustable strap (42) has a second buckle (56) and a means for engaging second buckle (57). Second buckle (56) can be of similar or different construction and design as first buckle (54).

Figure 2:
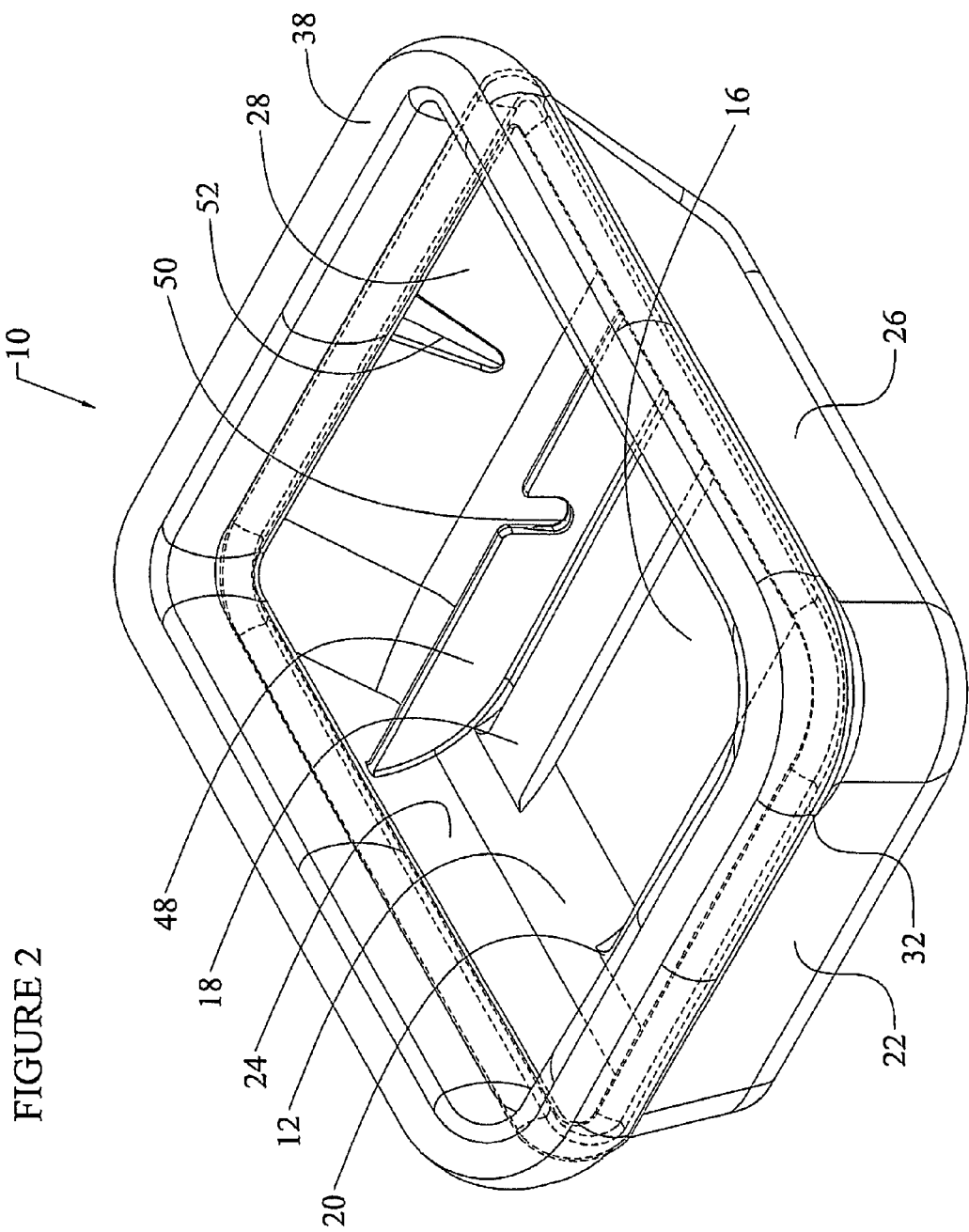
FIG. 2 depicts a perspective view of the inside surface of the flexible protective cover of FIG. 1.

Referring now to FIG. 2, a perspective view of an inside surface (16) of the present flexible protective cover depicted in FIG. 1 is shown.

FIG. 2 depicts the embodied flexible protective cover having one-piece flexible cover body (10) with central portion (12) having inside surface (16). Central portion (12) is connected to top edge (22), first side edge (24), second side edge (26), and angular edge (28). Angular edge (28) has opening (52) for securely engaging tubing or other medical equipment connected to an open epidermal site underneath one-piece flexible cover body (10).

Lip (32) is disposed on each of top edge (22), first side edge (24), second side edge (26), and angular edge (28). Sealing member (38) is shown disposed on lip (32) for creating a sealing engagement over an open epidermal site.

Inside surface (16) is shown having a first rib (18) and a second rib (20) for preventing deformation of one-piece flexible cover body (10). While FIG. 2 depicts two parallel ribs extending parallel to top edge (22), inside surface (16) can have any number of ribs that can be parallel, perpendicular, round, or shaped, and can extend wholly or partially across any dimension of one-piece flexible cover body (10).

A spacer (48) is also shown disposed on inside surface (16), for providing additional strength and resistance to deformation. Spacer (48) has a slit (50) for receiving tubing or medical equipment connected to an open epidermal site underneath one-piece flexible cover body (10). While FIG. 2 depicts one spacer (48), parallel to top edge (22) any number of spacers having any arrangement can be disposed on inside surface (16). It is also contemplated that spacer (48) can be omitted to provide additional space for very long, wide, or thick dressings or bandages, or when the additional strength and resistance provided by spacer (48) is not required.

Figure 3:
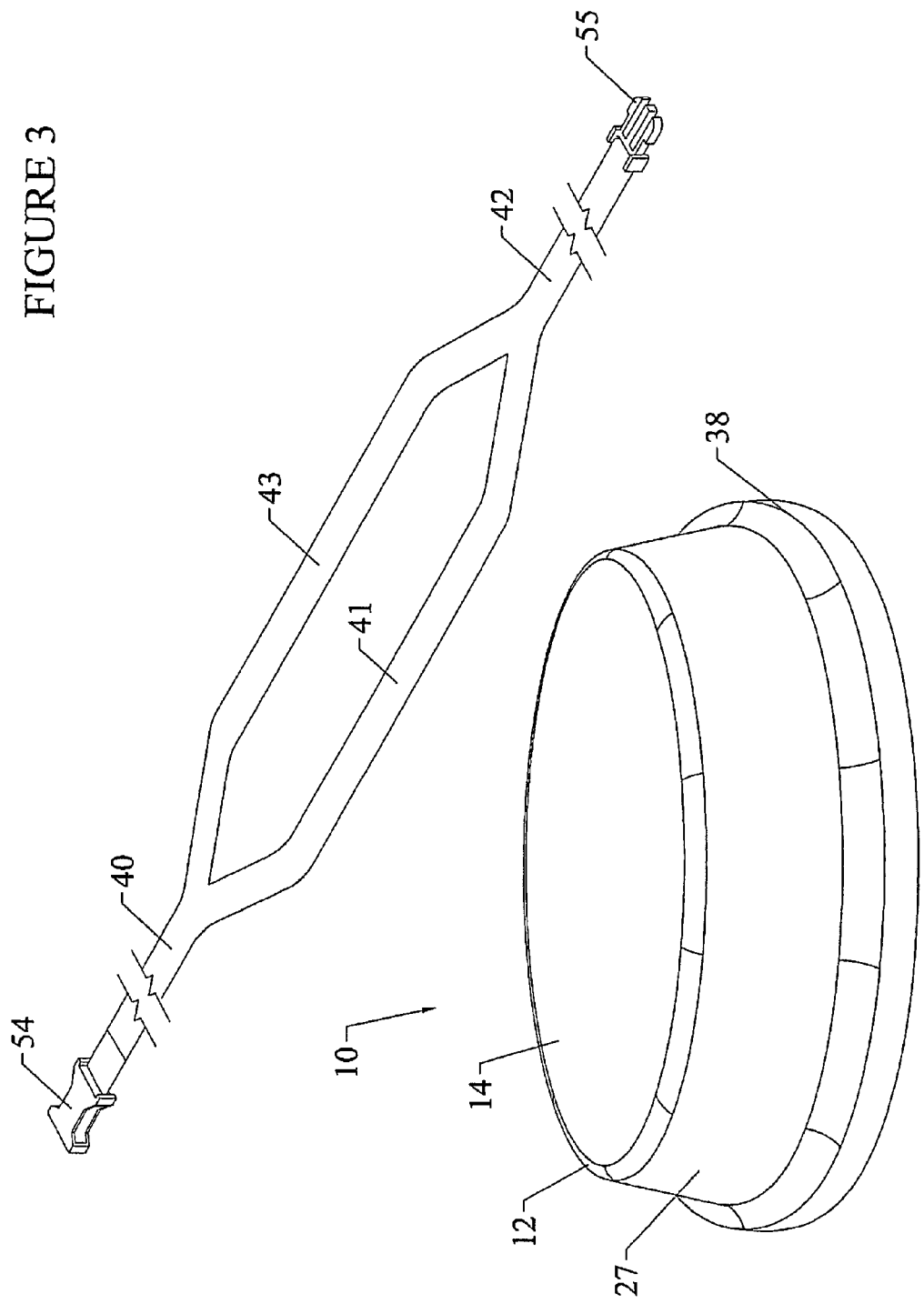
FIG. 3 depicts a perspective view of the outside surface of a flexible protective cover having a round one-piece flexible cover body.

Referring now to FIG. 3, a perspective view of an embodiment of the present flexible protective cover having a round one-piece flexible cover body (10) with a central portion (12) having outside surface (14) is shown.

Central portion (12) has an edge (27) connected substantially perpendicular to central portion (12). Edge (27) can also be connected to central portion (12) at an angle. It is also contemplated that portions of edge (27) could be connected substantially perpendicular to central portion (12), while other portions of edge (27) can be connected to central portion (12) at an angle.

Sealing member (38), which is depicted as flexible deformation resistant rubber, is shown disposed directly to edge (27) opposite central portion (12). In this depicted embodiment, it is contemplated that edge (27) can be made from a shapeable, bendable material, and central portion (12) can be made from a thin, shapeable material, such as a flexible plastic, rubber, or silicone barrier.

A first adjustable strap (40) is shown engaging a first fastening strap (41) and a second fastening strap (43). A second adjustable strap (42) is shown engaging the opposite ends of first fastening strap (41) and second fastening strap (43).

It is contemplated that first adjustable strap (40) and second adjustable strap (42) are used to secure the flexible protective cover over an open epidermal site, while first fastening strap (41) and second fastening strap (43) apply pressure to the outside surface (14) of one-piece flexible cover body (10) to create a seal between sealing member (38) and the open epidermal site.

First adjustable strap (40) is shown having first buckle (54), and second adjustable strap (42) is shown having means for engaging first buckle (55). While FIG. 3 depicts a single buckle, any number of buckles or other types of hook and loop fasteners, slidable fastening means, or elastic straps can be used.

Figure 4:
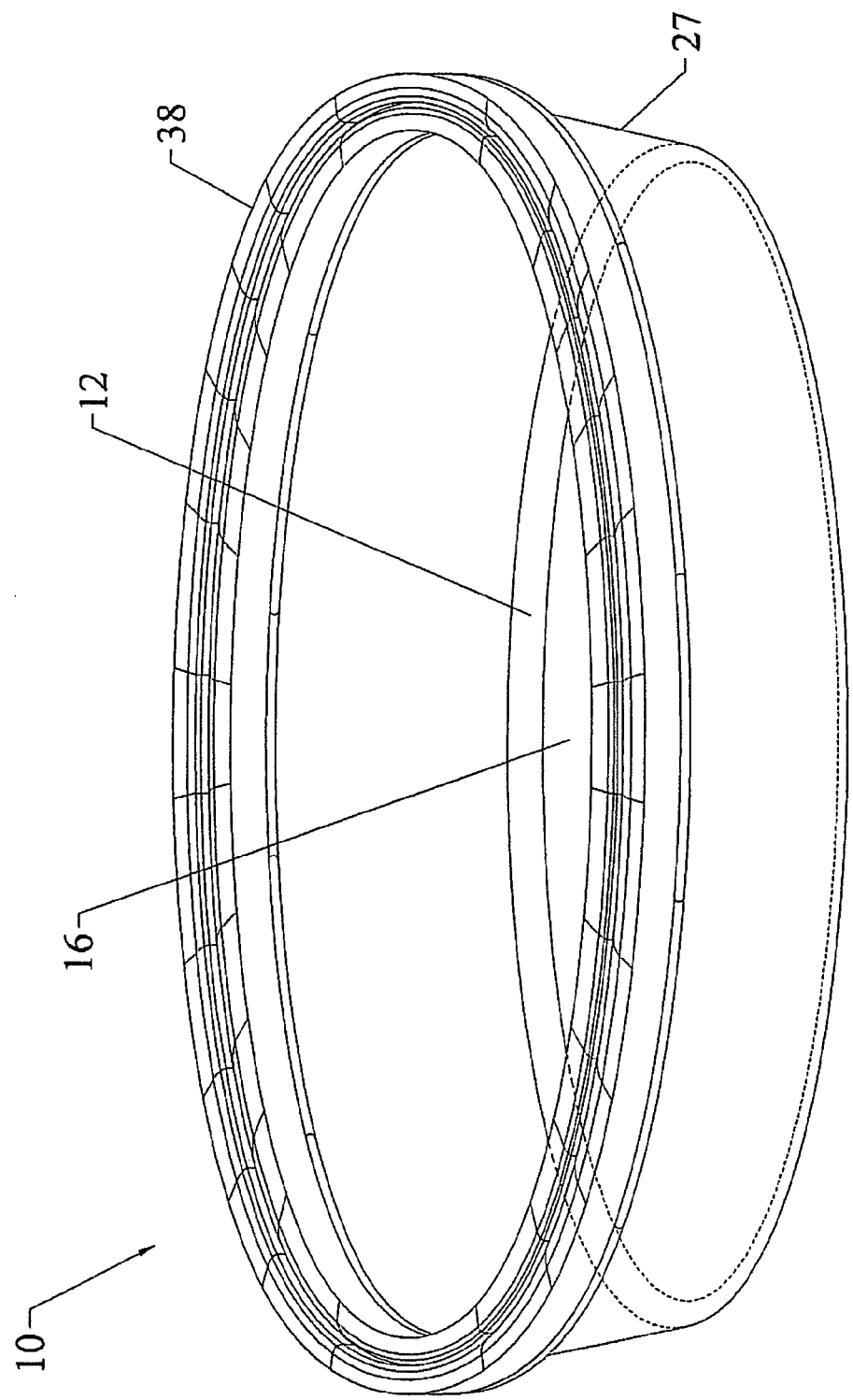
FIG. 4 depicts a perspective view of the inside surface of the flexible protective cover of FIG. 3.

Referring now to FIG. 4, a perspective view of the inside surface (16) of the flexible protective cover depicted in FIG. 3 is shown.

FIG. 4 depicts a round one-piece flexible cover body (10) having central portion (12) with inside surface (16). Edge (27) is connected substantially perpendicular to central portion (12). Sealing member (38) is disposed on edge (27). FIG. 4 depicts sealing member (38) as flexible, deformation resistant rubber, however, other types of sealing members, such as plastic-coated metal, inflatable tubing, deformation resistant tubing, and similar plastic, rubber, polymer, or other materials able to form a fluid-tight seal on a user are also contemplated.

Figure 5:
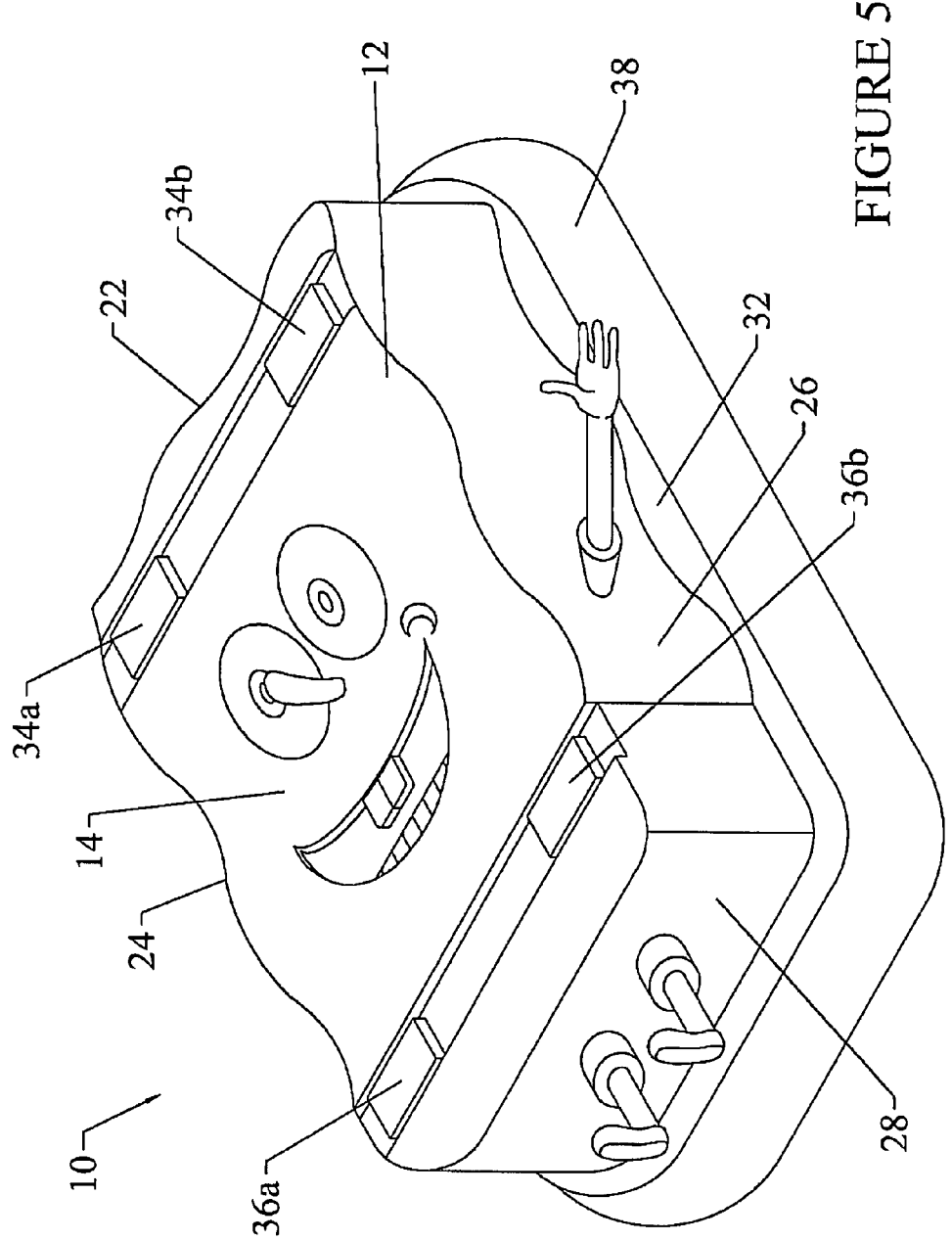
FIG. 5 depicts a perspective view of the outside surface of a flexible protective cover having a cartoon-shaped one-piece flexible cover body.

Referring now to FIG. 5, a perspective view of an embodiment of the present flexible protective cover having a cartoon-shaped one-piece flexible cover body (10) with a central portion (12) having outside surface (14) is shown.

The cartoon-shaped one-piece flexible cover body (10) has a top edge (22), a first side edge (24), a second side edge (26), and an angular edge (28), which encircle the perimeter of the central portion (12) and are connected substantially perpendicular to central portion (12). Depending on the shape of the cartoon-shaped one-piece flexible cover body (10), fewer than four edges can be used, such as a triangular shaped or round one-piece flexible cover body.

A lip (32) is disposed over top edge (22), first side edge (24), second side edge (26), and angular edge (28). Sealing member (38) is shown disposed over lip (32).

A first anchored portion (34a) and a second anchored portion (34b) of a first fastener, and a first anchored portion (36a) and a second anchored portion (36b) of a second fastener are shown disposed on outside surface (14), for receiving complementary fastener portions attached to adjustable straps.

Figure 6:
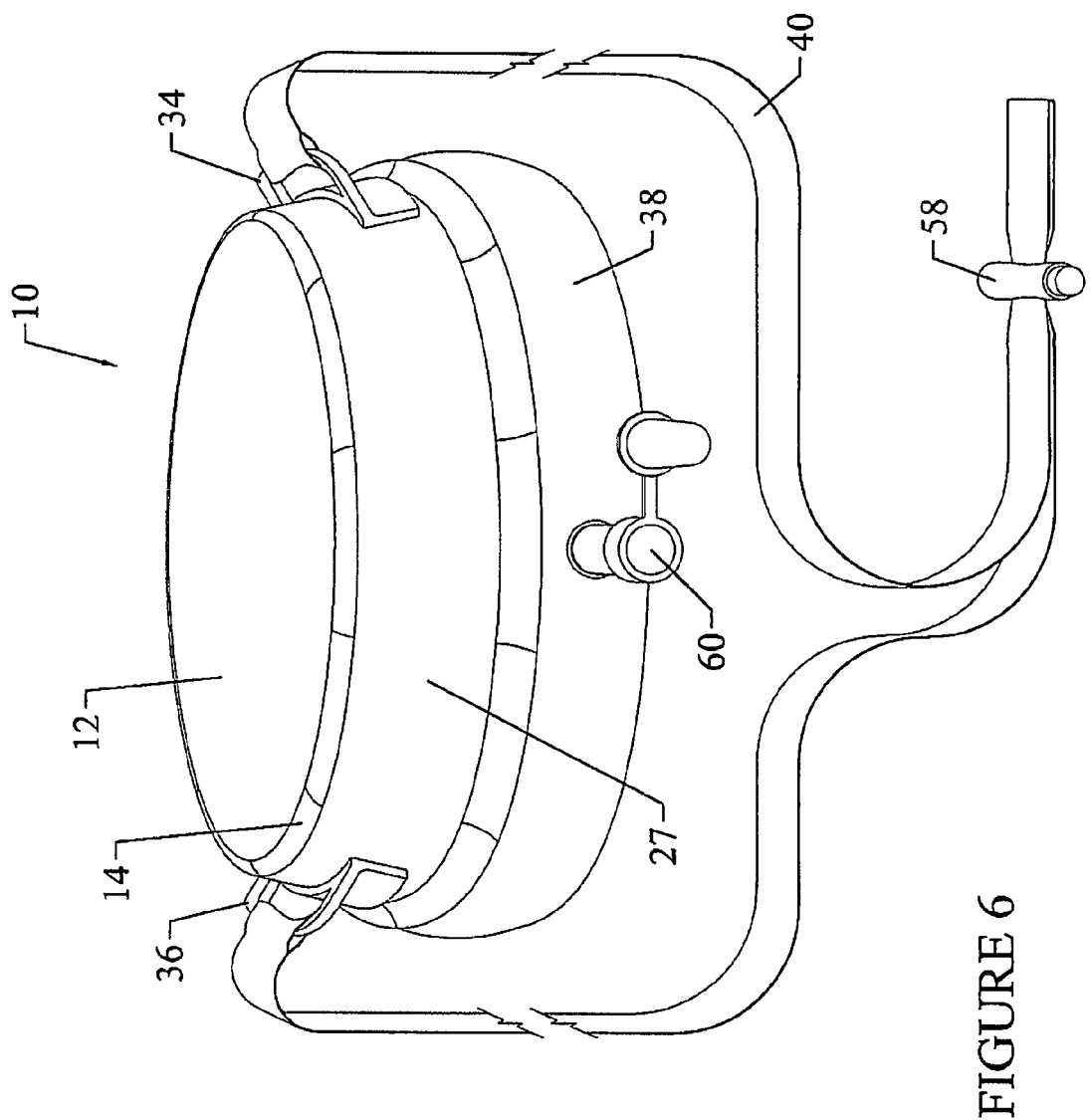
FIG. 6 depicts a perspective view of the outside surface of an alternative embodiment of the present flexible protective cover.

Referring now to FIG. 6, a perspective view of an alternative embodiment of the present flexible protective cover is depicted.

The embodied flexible protective cover has a one-piece flexible cover body (10) having a central portion (12) with an outside surface (14).

Central portion (12) has an edge (27) connected substantially perpendicular to central portion (12). A sealing member (38), is depicted disposed on edge (27). Sealing member (38) is depicted as inflatable tubing having a valve (60), however sealing member (38) can also include other sealing members, such as deformation-resistant tubing, and similar plastic, rubber, polymer, or other materials able to form a fluid-tight seal on a user. It is contemplated that valve (60) can be any type of valve, including a removable valve or a non-removable valve.

A first fastener (34) and a second fastener (36) are depicted integral with the central portion (12). While first fastener (34) and second fastener (36) are depicted as plastic loops molded to the central portion (12), other types of fasteners, such as hook and loop fasteners, reusable adhesive, and other similar fasteners are also contemplated.

A first adjustable strap (40) is shown engaging first fastener (34) and second fastener (36). A first adjustable strap (40) is contemplated to be an elastic material, however first adjustable strap (40) can also be a webbed material, a textile, a hypoallergenic material, or other similar materials.

A slidable fastener (58) is shown engaging first adjustable strap (40). It is contemplated that slidable fastener (58) can selectively engage and release first adjustable strap (40), such as through use of a switch or spring-actuated button, allowing slidable fastener (58) to move along first adjustable strap (40).

The movement of slidable fastener (58) allows first adjustable strap (40) to be tightened to cinch one-piece flexible cover body (10) to a user, forming a sealing engagement between sealing member (38) and an open epidermal site. Slidable fastener (58) can also be moved to loosen first adjustable strap (40) to allow removal of the flexible protective cover.

While these embodiments have been described with emphasis on the embodiments, it should be understood that within the scope of the appended claims, the embodiments might be practiced other than as specifically described herein.

What is claimed is:

1. A flexible protective cover for preventing fluid from entering an open epidermal site on a user, comprising:
   a. a one-piece flexible cover body for covering the open epidermal site, wherein the one-piece flexible cover body comprises:
      i. a central portion having an outside surface and an inside surface;
      ii. at least one edge connected to the central portion at an angle; and
      iii. a lip disposed around the edge;
   b. a sealing member disposed over the lip for providing a sealing engagement around the open epidermal site and preventing fluid from entering the open epidermal site;
   c. at least one adjustable strap removably connected to the outside surface over the one-piece flexible cover body, wherein the at least one adjustable strap secures the one-piece flexible cover body over the open epidermal site, applies pressure to the outside surface of the one-piece flexible cover body forming the sealing engagement, and secures the one-piece flexible cover body to the user, thereby eliminating the need for the use of adhesives; and
   d. wherein the central portion comprises at least one rib integrally molded to the inside surface for preventing deforming of the central portion.

2. The flexible protective cover of claim 1, further comprising at least one fastener having an anchored portion disposed on the outside surface of the central portion, wherein the at least one adjustable strap is removably connected to the anchored portion of the at least one fastener.

3. The flexible protective cover of claim 1, wherein the open epidermal site comprises a dressing, a catheter, an intravenous medical line, a surgical incision site, an intravenous line point of entry, a peripheral intravenous line point of entry, a port for central venous access, a central venous line point of entry, a catheter line point of entry, a boil, a blister, a wound, at least one suture, or combinations thereof.

4. The flexible protective cover of claim 1, wherein the one-piece flexible cover body is rectangular, round, oblong, elliptical, cartoon-shaped, polygon-shaped, or has the shape of an article.

5. The flexible protective cover of claim 1, wherein the one-piece flexible cover body comprises a non-irritating, non-toxic, hypoallergenic, recyclable, silicone based material.

6. The flexible protective cover of claim 1, wherein of the central portion further comprises at least one spacer integral with the inside surface.

7. The flexible protective cover of claim 6, wherein the at least one spacer comprises a slit for securely engaging tubing connected to the open epidermal site.

8. The flexible protective cover of claim 1, wherein the edge further comprises at least one opening for engaging in a force fit, tubing connected to the open epidermal site.

9. The flexible protective cover of claim 1, wherein the sealing member is a member of the group consisting of: a deformation resistant tubing that can reassume shape after light compression, an inflatable tubing comprising at least one valve that can be used to inflate the inflatable tubing after compression to seal gaps between the central portion and the open epidermal site, at least one strip of shapeable material that retains a shape after bending, or combinations thereof.

10. The flexible protective cover of claim 1, wherein the edge comprises a shapeable plastic that retains a shape after bending.

11. The flexible protective cover of claim 1, wherein the at least one adjustable strap comprises at least one buckle for enabling the at least one adjustable strap to be cinched to the user, at least one slidable fastener connected to the adjustable strap, or combinations thereof.

12. The flexible protective cover of claim 1, wherein at least two adjustable straps further engage a first fastening strap and a second fastening strap, wherein the first and second fastening straps engage the at least one fastener.

13. The flexible protective cover of claim 1, further comprising at least two edges, wherein at least one of the edges is connected substantially perpendicular to the central portion, and at least a second edge is connected to the central portion at the angle.

14. A flexible protective cover for preventing fluid from entering an open epidermal site on a user, comprising:
   a. a one-piece flexible cover body for covering the open epidermal site, wherein the one-piece flexible cover body comprises:
      i. a central portion having an outside surface and an inside surface; and
      ii. at least one edge connected to the central portion at an angle;
   b. an inflatable sealing member integral with the edge and providing a sealing engagement between the one-piece flexible cover body and the open epidermal site for preventing fluid from entering the open epidermal site; and
   c. at least one adjustable strap removably connected to the outside surface, wherein the at least one adjustable strap secures the one-piece flexible cover body over the open epidermal site, applies pressure to the one-piece flexible cover body forming the sealing engagement, and secures the one-piece flexible cover body to the user, thereby eliminating the need for the use of adhesives.

15. The flexible protective cover of claim 14, further comprising at least one fastener integral with the outside surface of the central portion, wherein the at least one adjustable strap is removably connected to the at least one fastener.

16. The flexible protective cover of claim 14, wherein the one-piece flexible cover body comprises a non-irritating, non-toxic, hypoallergenic, recyclable, silicone based material.

17. The flexible protective cover of claim 14, wherein the central portion comprises at least one rib integrally molded to the inside surface for preventing deformation of the central portion.

18. The flexible protective cover of claim 14, wherein of the central portion further comprises at least one spacer integral with the inside surface.

19. The flexible protective cover of claim 18, wherein the at least one spacer comprises a slit for securely engaging tubing connected to the open epidermal site.

20. The flexible protective cover of claim 14, wherein the edge further comprises at least one opening for engaging in a force fit, tubing connected to the open epidermal site.

21. The flexible protective cover of claim 14, wherein the inflatable sealing member is a member of the group consisting of: a deformation resistant tubing that can reassume shape after light compression, an inflatable tubing comprising at least one valve that can be used to inflate the inflatable tubing after compression to seal gaps between the one-piece flexible cover body and the open epidermal site, or combinations thereof.

22. The flexible protective cover of claim 14, wherein the at least one adjustable strap comprises at least one buckle for enabling the at least one adjustable strap to be cinched to the user, at least one slidable fastener connected to the adjustable strap, or combinations thereof.

23. The flexible protective cover of claim 14, wherein at least two adjustable straps further engage a first fastening strap and a second fastening strap, wherein the first and second fastening straps engage the at least one fastener.

24. The flexible protective cover of claim 14, further comprising at least two edges, wherein at least one of the edges is connected substantially perpendicular to the central portion, and at least a second edge is connected to the central portion at an angle.

25. A flexible protective cover for preventing fluid from entering an open epidermal site on a user, comprising:
   a. a one-piece flexible cover body for covering the open epidermal site, wherein the one-piece flexible cover body comprises:
      i. a central portion having an outside surface and an inside surface;
      ii. at least one edge connected to the central portion at an angle substantially perpendicular to the central portion; and
      iii. a lip disposed around the edge, wherein the one-piece flexible cover body has a first thickness;
   b. a sealing member disposed over the lip for providing a single continuous sealing engagement around the open epidermal site and preventing fluid from entering the open epidermal site, wherein the sealing member has a thickness greater than the first thickness of the one-piece flexible cover body;
   c. at least one adjustable strap removably connected to the outside surface over the one-piece flexible cover body, wherein the at least one adjustable strap secures the one-piece flexible cover body over the open epidermal site, applies pressure to the outside surface of the one-piece flexible cover body forming the sealing engagement, and secures the one-piece flexible cover body to the user, thereby eliminating the need for the use of adhesives;
   d. wherein the central portion comprises at least one rib integrally molded to the inside surface for preventing deforming of the central portion; and
   e. wherein the edge further comprises at least one opening for engaging in a force fit, tubing connected to the open epidermal site.

* * * * *